United States Patent [19]

Wada et al.

[11] Patent Number: 5,951,994
[45] Date of Patent: Sep. 14, 1999

[54] PESTICIDAL COMPOSITIONS IN PASTE FORM

[75] Inventors: Yuzuru Wada, Hachioji; Yuichi Otsu, Tochigi; Kunihiro Isono, Shimotsuga-gun; Shigeharu Koyama, Tochigi; Shinzaburo Sone, Ibaraki, all of Japan

[73] Assignee: Nihon Bayer Agrochem K. K., Tokyo, Japan

[21] Appl. No.: 08/938,479

[22] Filed: Sep. 30, 1997

Related U.S. Application Data

[63] Continuation of application No. 08/395,557, Feb. 28, 1995, abandoned.

[30] Foreign Application Priority Data

Mar. 4, 1994 [JP] Japan ........................................ 6-58344

[51] Int. Cl.⁶ .......................... A01N 25/00; A01N 25/02; A01N 25/08
[52] U.S. Cl. .......................... 424/405; 424/409; 514/937; 514/772
[58] Field of Search .................................. 424/405, 409; 514/937, 772

[56] References Cited

U.S. PATENT DOCUMENTS

| | | | |
|---|---|---|---|
| 5,126,139 | 6/1992 | Geary | 424/410 |
| 5,164,179 | 11/1992 | Hioki et al. | 424/78.08 |
| 5,354,565 | 10/1994 | Iwasaki et al. | 424/605 |
| 5,468,747 | 11/1995 | Clough et al. | 424/632 |
| 5,645,845 | 7/1997 | Neumann et al. | 424/405 |
| 5,683,826 | 11/1997 | Poncelet et al. | 428/702 |
| 5,705,175 | 1/1998 | Johnson | 424/409 |
| 5,759,561 | 6/1998 | Angst et al. | 424/407 |
| 5,762,949 | 6/1998 | Kern | 424/405 |

FOREIGN PATENT DOCUMENTS

| | | |
|---|---|---|
| 0 430 633 A1 | 6/1991 | European Pat. Off. . |
| 0 564 945 A1 | 10/1993 | European Pat. Off. . |
| 62042902 | 2/1987 | Japan . |
| WO 93/12652 | 7/1993 | WIPO . |
| WO 93/14167 | 7/1993 | WIPO . |
| WO 93/21763 | 11/1993 | WIPO . |

OTHER PUBLICATIONS

Derwent Publication 87–091,468; Abstract of JP–A–62 042 902.
Chemical Abstracts, vol. 88, No. 17, 79:1219 (1973).
Chemical Abstracts, vol. 117, No. 25, 117:247121 (1992).
Chemical Abstracts, vol. 95, No. 21, 95:182262 (1981).
The Pesticide Manual, 10th Ed., pp. 1000–1001.
Protecçao das plantas, Manual de Utilizaçao BAYER (Plant Protection User's Manual BAYER) p. 92.
Derwent Abstract of JP 62–270,502 (1987).
Derwent Abstract of JP 62–42, 902 (1987).
Derwent Abstract of JP 50–94, 120 (1975).

*Primary Examiner*—Robert H. Harrison
*Attorney, Agent, or Firm*—Sprung Kramer Schaefer & Briscoe

[57] ABSTRACT

Novel pasty compositions for the control of animal pests and fungal diseases on plants, which compositions comprise at least one pesticidally active or fungicidally active compound and at least one adjuvant, which is solid, liquid or pasty at room temperature and optionally, one or more excipients and water.

5 Claims, No Drawings

PESTICIDAL COMPOSITIONS IN PASTE FORM

This application is a continuation, of application Ser. No. 08/395,557 filed Feb. 28, 1995 now abandoned.

The present invention relates to new pasty compositions for the control of animal pests and fungal diseases on plants.

There are two application methods, which hitherto have been mostly employed for the control of fungal diseases on plants or animal pests infesting the plants. The first method comprises applying the active ingredients by spraying liquid formulations or solid formulations in pulverized form onto the outer surface of the plants to be treated. The second method consists in mixing liquid or solid formulations of the active ingredients with the soil adjacent to the roots of the plants to be treated.

When working according to the spraying technique, the sprayed active ingredients reach the animal pests and/or the disease-causing fungi at a fast rate so that this method is featured by being a fast acting one. However, a disadvantage of this method is that the major part of the sprayed active ingredients generally deposits on the soil and then drifts away from the treated zones leaving a rather low dosage of the active ingredients on the plants. Further, there is not a less risk that the operators, who are spraying the formulations, become exposed to the chemicals during spraying the formulations.

Upon working according to the second of the two above-mentioned methods, i.e. mixing formulations with the soil, the risk of becoming contaminated with chemicals is markedly reduced for the operators, who are applying the formulations. However, this method suffers from the disadvantage that the desired effect can only be achieved, if active ingredients having systemic properties are used in the treatment. As compared with the application by means of spraying, the mixing technique is giving rise to the demerits that the biological effect of the active ingredients emerges at a slower pace, the effective amounts of the active ingredients in the treatment become smaller due to absorption of the active ingredients in the soil and to drifting away by sprinkling with water, and a higher risk of a prolonged residual toxicity in the soil is inherent.

Considering the above-said, it is highly desirable to develop a novel control technique avoiding the above-mentioned disadvantages by using the active ingredients in an amount as small as possible and still maintaining a biological effect as high as possible.

Further, there has already been devised a method for the protection of trees, which method consists in boring a hole into the body of the tree and then injecting a liquid formulation of biologically active ingredients into the hole so that the formulation gradually penetrates into the interior of the tree like a transfusion of medicine for human beings. However, this method requires for the liquefaction of the active ingredients a great amount of solvents and/or surface active agents, which may be toxic to trees. In such treatment, the volumes of the liquid formulations applied for the protection of the trees inevitably become greater. Thus, the operators have to wait for a prolonged period of time until the penetration of the liquid formulations into the trees is complete. After the treatment, it is also necessary to recover the containers initially comprising the liquid formulations, which means that the working efficiency is poor. If great amounts of phytotoxic solvents and surface active agents are injected into the trees, the tissue of the tree bodies may collapse along the direction of longitudinal growing thereby hindering the circulation of water in the tissue, and further the injected liquids may cause an extensive collapse in plant body-forming layers that are located in the vicinity of the treated sites and are important for the growth of the trees. This may result in serious damages on the trees, such as extensive cleavages on the surface of the trees and so on. Consequently, it is highly desirable to develop a method of treatment, which can be carried out within a short period of time and which is not only entirely free from a risk for the operators of becoming exposed to the chemicals but also free from any phyto-toxicity causing a growth inhibition of trees.

There have now been found new pasty compositions for the control of animal pests and fungal diseases on plants, which compositions comprise at least one pesticidally active or fungicidally active compound and at least one adjuvant, which is solid, liquid or pasty at room temperature, and optionally, one or more excipients and water.

It has also been found that the compositions according to the invention can be used effectively for the control of animal pests and fungicidal diseases on plants by treating the surfaces of the plants with said compositions.

It is decidedly surprising that the compositions according to the invention are outstandingly effective for the control of animal pests and fungal diseases on plants, since it could not be foreseen that the compositions are suitable for causing a sufficient penetration of the active ingredients into the plants.

When the pasty compositions according to the invention are applied onto plant bodies, the compositions exhibit an assured controlling effect on fungal diseases infecting plants and on animal pests infesting the plants, even if the active compounds are used in a far smaller amount than that to be used in the conventional spray application. Further the compositions guarantee an effective control and do almost completely eliminate an undesired release of the active compounds to the environment. After all, there is no risk for the operators of becoming exposed to dusts or sprays of chemicals. Thus, the present invention provides epoch-making compositions having a high-grade safety.

The compositions according to the invention do contain at least one pesticidally active or fungicidally active compound. Pesticidal compounds in the present context are compounds, which are suitable for the control of insects, acarides and/or nematodes infesting plants. Fungicidal compounds in the present context are compounds, which are suitable for combating fungal diseases infecting plants. The compositions according to the invention may contain any pesticidal or fungicidal compound having systemic properties.

The pasty compositions according to the invention preferably contain one or more of the following pesticidally active or fungicidally active compounds:

1-(6-chloro-3-pyridylmethyl)-N-nitro-imidazolidin-2-ylideneamine,

N-cyano-N'-(2 chloro-5-pyridylmethyl)-N'-methyl acetoamidine,

1-[N-(6-chloro-3-pyridylmethyl)-N-ethyl amino]-1-methylaamino-2-nitroethylene, 1-(2-chloro-5-pyridylmethyl)-3,5-dimethyl-2-nitroimino-hexahydro-1,3,5-triazine, 1-(2-chloro-5-thi azolylmethyl)-3,5-dimethyl-2-nitroimino-hexahydro-1,3,5-triazine, O,O-dimethyl O-3-methyl-4-(methylsulfinyl)-phenyl phosphorothioate, trans-1,4,5,6-tetrahydro-1-methyl-2-[2-(3-methyl-2-thienyl)-vinyl]-pyrimidine tartrate, (−)-(S)-2,3,5,6-tetrahydro-6-phenylirnidazo[2,1-b] thiazole hydrochloride, 1-(4-chlorophenoxy)-3,3-dimethyl-1-(1,2,4-triazol-1-yl)-2-butanone, all-rac-1-(biphenyl-4-yloxy)-3,3-dimethyl-1-(1 H-1,2,4-triazol-1-yl)-butan-2-ol, 2-p-chlorophenyl-2-(1 H-1,2,4-triazol-1-yl-methyl)-hexane nitrile, (R,S)-2-(2,4-dichlorophenyl)-1-(1 H-1,2,4-triazol-1-yl)-hexan-2-ol, 1-[2-(2,4-dichlorophenyl)-4-propyl-1,3-dioxolan-2-yl-methyl]-1 H-1,2,4-triazole, (E)-4-chloro-α,α,α-trifluoro-N-(1-imidazol-1-yl-2-propoxyethylidene)-O-toluidine, N-propyl-N-[2-(2,4,6-trichlorophenoxy)-ethyl]-imidazol-1-yl carboxamide, pent-4-enyl N-furfuryl-N-imidazol-1-yl carbonyl-DL-homoalaninate, 2,4'-dichloro-α-(pyrimidin-5-yl)-benzhydryl alcohol, (E)-(R,S)-1-(4-chlorophenyl)-4,4-dimethyl-2-(1 H-1,2,4-triazol-1-yl)-1-pentene-3-ol, (E)-(S)-1-(4-chlorophenyl)-4,4-dimethyl-2-(1 H-1,2,4-triazol-1-yl)-penta-1-ene-3-ol, (R,S)-1-(4-chlorophenyl)-4,4-dimethyl-3-(1 H-1,2,4-triazol-1-ylmethyl)-pentan-3-ol, 2',4'-dichloro-2-(3-pyridyl)-acetophenone (E,Z)-O-methyloxime, 1,4-bis-(2,2,2-trichloro-1-formarnidoethyl)-piperazine, (2RS,3RS)-1-(4-chlorophenyl)-4,4-dimethyl-2-(1 H-1,2,4-triazol-1-yl)-pentan-3-ol, (+)-cis-4-[3-(4-tert-butylphenyl)-2-methylpropyl]-2,6-dimethylmorpholine, and 2-(4-fluorophenyl)-2-(1,2,4-triazol-2-ylmethyl)-3-(2-chlorophenyl)-epoxyethane.

The pasty compositions according to the invention do contain at least one adjuvant, which is solid, liquid or pasty at room temperature. Such adjuvants preferably are selected from fatty acid polyhydric alcohol esters, polyalkylene oxide addition products of fatty acid polyhydric alcohol esters, polyalkylene oxide fatty acid esters, polyalkylene oxide lanolins, sorbitol lanolin derivatives, polyalkylene oxide bees wax, sorbitol bees wax derivatives, polysaccharides, polysaccharide derivatives, higher alcohols having at least eight carbon atoms, polyalkylene oxides, graft polymers of polyalkylene oxides, block copolymers of polyalkylene oxides, and random polymers of polyalkylene oxides.

As examples of such adjuvants, there may be mentioned fatty acid polyhydric esters, such as sorbiton monolaurate, sorbitan monooleate, sorbitan trioleate, etc., polyalkylene oxide addition products of fatty acid polyhydric alcohols esters, such as polyoxyethylene sorbitan monolaurate, polyoxyethylene sorbitan monooleate, and polyoxyethylene sorbitan tristearate, etc., polyalkylene oxide fatty acid esters, such as polyoxyethylene laurate, polyoxyethylene oleate, and polyoxyethylene stearate, etc., polysaccharides, such as starch, cellulose, sucrose, natural rubber, carboxymethyl cellulose, methyl cellulose, and sucrose stearate, etc., higher alcohols, such as lauryl alcohol, etc., polyalkylene oxides, their graft polymers and their block polymers and random polymers, such as polyethylene glycol, polypropylene glycol, polyglycerine, polyoxyethylene-polyoxypropylene block polymer and polyoxyethylene polyoxypropylene block polymer glycerine ether, etc.

As further examples of the adjuvants, there may be mentioned sorbitan monolaurate, polyoxyethylene sorbitan monolaurate, polyethylene glycol oleate, polyoxyethylene lanolin, polyethylene bees wax, polyethylene glycol (#200), polyethylene glycol (#400), polyethylene glycol (#1000), and cellulose.

The pasty compositions according to the invention may optionally contain one or more excipients and water, said excipients being generally employed in the form of powdery solid materials.

As the examples of such excipients, there may be mentioned lignin, lignin derivatives and mineral materials, such as clay, talc, amorphous silicon dioxide and the like.

The concentration of the pesticidally active or fungicidally active compounds in the pasty compositions according to the invention can be varied within a certain range. In general, the compositions contain from about 1 to about 50 parts by weight of one or more pesticidally active or fungicidally active compounds per 100 parts by weight of the composition.

The concentration of adjuvants in the compositions according to the invention can also be varied within a certain range. In general, the compositions contain from about 50 to about 99 parts by weight of one or more adjuvants, optionally in admixture with one or more excipients and/or water, per 100 parts by weight of the composition.

The pasty compositions according to the invention are prepared by known, conventional methods of manufacturing pastes. In general, predetermined amounts of pesticidally active or fungicidally active compounds, adjuvants and, if necessary, of excipients and/or water are thoroughly mixed so as to form a pasty formulation.

All mixing apparatuses conventionally suitable for this purpose can be employed for the preparation of the pasty compositions according to the invention. The use of high-speed shearing mixers is preferred.

Upon using the pasty compositions according to the invention for practically controlling animal pests or fungal diseases on plants, said pasty compositions are coated on either plant body surfaces or cutout openings formed thereon. Alternatively, the pasty compositions can also be filled into bored openings formed by a boring drill, so as to attain the aimed purpose.

Further, as one of the operating modes of such coating, a band-shape stripe with a pasty composition according to the invention having been precoated thereon is bound around a plant to be treated.

The pasty compositions according to the invention can be generally applied to control all kinds of animal pests infesting plants. As examples of insects, there may be mentioned from the order of Coleoptera, e.g. Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica spp., Monochamus alternatus, Lissorhoptrus oryzophilus, Lyctus bruneus;

from the order of Lepidoptera, e.g., Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella;

from the order of Hemiptera, e.g. Nephotettix cincticeps, Nilaparvata lugens, Pseudococcus comstocki, Unaspis yanonensis, Myzus persicae, Aphis pomi, Aphis gossypii, Rhopalosiphum pseudobrassicas, Stephanitis nashi, Nezara spp., Cimex lectularius, Trialeurodes vaporariorum, Psylla spp.;

from the order of Orthoptera, e.g. Blatella germanica, Periplaneta americana, Gryllotalpa africana, Locusta migratoria migratoriodes;

from the order of Isoptera, e.g. Reticulitermes speratus, Coptotermes formosanus;

from the order of Azaminura, e.g. Thrips palmi Karny;

from the order of Diptera, e.g. Musca domestica, Aedes aegypti, Hylemia platura; Celux pipiens, Anopheles silnensis, Culex tritaeniorhynchus.

As examples of mites, there may be mentioned Tetranychus telarius, Tetranychus urticae, Panonychus citri, Aculops pelekassi, Tarsonemus spp., and the like.

As examples of nematodes, there may be mentioned Meloidogyne incognita, Bursaphelenchus lignicolus Mamiya et Kiyohara, Aphelenchoides besseyi, Heterodera glycines, Pratylenchus spp., and the like.

The pasty compositions according to the invention can also be generally applied to control all kinds of fungal diseases infecting plants. As examples of such fungal diseases, there may be mentioned various plant blights caused by Plasmo-diophoromycetes, Oomycetes, Chytridiomycetes, Zygomycetes, Ascomycetes, Basidiomycetes, Deuteromycetes, and those caused by Pseudomonodaceae, Rhizobiaceae, Enterobacteriaceae, Corynebacteriaceae and Streptomyceteceae.

The pasty formulations according to the invention can be generally applied to all common plants. Preferably, the compositions can be applied to fruit vegetables, flowers and ornamental plants and trees such as, for example, tomatoes, eggplants, cucumbers, roses, chrysanthemum, pine trees (black pines, red pines, larches), common spruce, Japanese cedars, Japanese cypresses and so on; further Hiba cypresses, chestnut trees, apple trees, pears, peaches, plums, cherry trees, persimmon and so on.

The preparation of the compositions according to the invention and the use of such compositions for the control of animal pests and fungal diseases on plants are illustrated by the following examples. The technical scope of the invention, however, is not limited by the examples to any extent.

EXAMPLES

Examples of pesticidally active components in the pasty compositions:

Imidacloprid: 1-(6-chloro-3-pyridylmethyl)-N-nitro-imidazolidin-2-ylideneamine,

Triadimefon: 1-(4-chlorophenoxy)-3,3-dimethyl-1-(1,2,4-triazol-1-yl)-2-butanone, Mesulfenfos: O,O-dimethyl O-3-methyl-4-(methylsulfinyl)-phenyl phosphorothioate, Morantel tartrate: Trans-1,4,5,6-tetrahydro-1-methyl-2-[2-(3-methyl-2-thienyl)-vinyl-pyrimidine tartrate, Levamisol hydrochloride: (−)-(S)-2,3,5,6-tetrahydro-6-phenylimidazo[2, 1-b]-thiazol hydrochloride, Compound A N-cyano-N'-(2 chloro-5-pyridylmethyl)-N'-methyl acetoamidine, Compound B 1-[N-(6-chloro-3-pyridylmethyl)-N-ethyl-amino]-1-methylamino-2-nitroethylene.

The pasty compositions according to the following examples are prepared by intimately mixing the components in the stated amounts by means of a high-speed shearing mixer.

|  |  | (parts by weight) |
|---|---|---|
| Example 1 | Imidacloprid | 10 |
|  | Sorbitan monolaurate | 90 |
| Example 2 | Imidacloprid | 10 |
|  | Polyoxyethylene sorbitan monolaurate | 90 |
| Example 3 | Triadimefon | 1 |
|  | Polyethylene glycol oleate | 99 |
| Example 4 | Imidacloprid | 10 |
|  | Triadimefon | 1 |
|  | Polyoxyethylene lanolin | 89 |
| Example 5 | Imidacloprid | 10 |
|  | Triadimefon | 1 |
|  | Polyoxyethylene bees wax | 89 |
| Example 6 | Triadimefon | 1 |
|  | Polyethylene glycol (#200) | 84 |
|  | Polyoxyethylene sorbitan monolaurate | 15 |
| Example 7 | Mesulfonfos | 50 |
|  | Polyethylene glycol (#1000) | 40 |
|  | Polyoxyethylene sorbitan monolaurate | 10 |
| Example 8 | Mesulfonfos | 50 |
|  | Polyethylene glycol (#400) | 35 |
|  | Cellulose powder | 10 |
|  | Amorphous silicon dioxide | 5 |
| Example 9 | Mesulfenfos | 50 |
|  | Sorbitan monolaurate | 35 |
|  | Cellulose powder | 10 |
|  | Amorphous silicon dioxide | 5 |
| Example 10 | Imidacloprid | 10 |
|  | Polyethylene glycol (#1000) | 40 |
|  | Polyoxyethylene sorbitan monolaurate | 50 |
| Example 11 | Compound A | 10 |
|  | Polyethylene glycol (#1000) | 40 |
|  | Polyoxyethylene sorbitan monolaurate | 50 |
| Example 12 | Compound B | 10 |
|  | Polyethylene glycol (#1000) | 40 |
|  | Polyoxyethylene sorbitan monolaurate | 50 |
| Example 13 | Imidacloprid | 5 |
|  | Polyethylene glycol (#1000) | 50 |
|  | Sorbitan monolaurate | 45 |
| Example 14 | Imidacloprid | 5 |
|  | Polyethylene glycol (#1000) | 50 |
|  | Polyoxyethylene sorbitan monolaurate | 45 |
| Example 15 | Imidacloprid | 5 |
|  | Polyethylene glycol (#1000) | 25 |
|  | Polyethylene glycol (#4000) | 25 |
|  | Sorbitan monolaurate | 45 |
| Example 16 | Imidacloprid | 5 |
|  | Polyethylene glycol (#1000) | 25 |
|  | Polyethylene glycol (#4000) | 25 |
|  | Polyoxyethylene sorbitan monolaurate | 45 |
| Example 17 | Imidacloprid | 5 |
|  | Triadimefon | 1 |
|  | Polyethylene glycol (#1000) | 84 |
|  | Sorbitan monolaurate | 10 |
| Example 18 | Imidacloprid | 5 |
|  | Polyethylene glycol (#1000) | 90 |
|  | Sorbitan monolaurate | 5 |
| Example 19 | Imidacloprid | 5 |
|  | Polyethylene glycol (#1000) | 85 |
|  | Polyoxyethylene sorbitan monolaurate | 10 |

USE EXAMPLES

Example A Efficacy test on pine trees against pine wood nematoda

Test compounds a: Mesulfenfos b: Levamisol (hydrochloride)

c: Morantel tartrate

A paste-form formulation described in Example 8 was prepared from each of the above-mentioned compounds.

Test tree: Black pine trees (15 years old)

Application method: Holes (6 mm in diameter) were bored into the trees using a drill at the breast height. The past-form formulation was filled into the holes with the applicator.

Date of application: Early summer, in the middle of June.

Inoculation method: The holes (4 mm in diameter, 1 cm in depth) were bored into the testing trees and 15,000 heads of the pine wood nematoda were artificially inoculated in each hole. The inoculation was carried out in three holes in total, viz. two holes in the upper part of the brunch and one hole in the trunk. The total number of the nematoda inoculated amounted to 45,000 per tree.

Date of inoculation: Thirty days after the application.

Evaluation method: Resin forming state was rated according to the ODA method.

Date of evaluation: Two months after the inoculation.

The scale of resin forrning state

The test results are shown in Table 1.

TABLE 1

| Formulation under Test | Tree dia. at the breast height (cm) | Height of trees (m) | Dosage of active ingredient (g) | Evaluated ratings | |
| --- | --- | --- | --- | --- | --- |
| | | | | Before inoculation | Two months after inoculation |
| a | 14 | 6 | 3.5 |  |  |
| a | 14.5 | 6 | 1.5 |  |  |
| b | 14.5 | 5.5 | 5.6 |  | 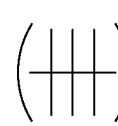 |

TABLE 1-continued

| | | | | Evaluated ratings | |
|---|---|---|---|---|---|
| Formulation under Test | Tree dia. at the breast height (cm) | Height of trees (m) | Dosage of active ingredient (g) | Before inoculation | Two months after inoculation |
| c | 14 | 5 | 5.6 | ||||  ||| | ||||  ||| |
| Untreated | 14 | 5 | — | ||||  ||| | ||||  ○  — |

Note: The above-stated results were obtained based on an average evaluation of seven test trees per one test ward.

Example B Efficacy tests on vegtables against aphids
Formulations: Pasty formulations were prepared by intimately mixing the components in the stated amounts.
The present invention:

| | | (parts by weight) |
|---|---|---|
| Paste I: | Imidacloprid | 10 |
| | Sorbitan monolaurate | 90 |
| Paste II: | Imidacloprid | 10 |
| | Polyoxyethylene sorbitan monolaurate | 90 |
| Paste III: | Imidacloprid | 10 |
| | Polyethylene glycol (#1000) | 40 |
| | Polyoxyethylene sorbitan monolaurate | 50 |
| Paste IV: | Compound A | 10 |
| | Polyethylene glycol (#1000) | 40 |
| | Polyoxyethylene sorbitan monolaurate | 50 |
| Paste V: | Compound B | 10 |
| | Polyethylene glycol (#1000) | 40 |
| | Polyoxyethylene sorbitan monolaurate | 50 |

Comparison:

| | | (parts by weight) |
|---|---|---|
| Comparative Example 1: | Imidacloprid Polyoxyethylene laurylether | 10 90 |
| Comparative Example 2: | Imidacloprid Polyoxyethylene nonylphenyl-ether | 10 90 |
| Comparative Example 3: | Imidacloprid Vaseline | 10 90 |

Tested crops: Cucumber (var. Suyo) and eggplant (var. Senryo ni gou) The vegetables at the growth stage of 8 leaves were used in this test.

Pest species: Aphis gossypii (wild strain) for cucumber and Myzus persicae (organophosphorus and carbamate insecticides resistant strain) for eggplant were used in this test.

Plot size and replications: Two plants planted in one pot (15 cm in diameter) per plot and two replications.

Date of application: In the beginning of October.

Application method: About 200 heads of Aphis gossypii or 120 heads of Myzus persicae were attached artificially on each test plant one day before the application. The test formulations put on an aluminium foil were wound on the test plant.

Evaluation method: Before the application and 7 days, 14 days and 21 days after the application, the numbers of aphids infesting the test plants were counted. After every evaluation, about 100 heads of aphids were further attached on the test plants. Phytotoxicity was also evaluated and rated from 0 to 5 at the day of evaluation.

Scale for the evaluation of the phytotoxicity:

0: No phytotoxicity
1: Sligh necrosis on leaf margin or slight leaf spotting
2: necrosis on leaf margin or leaf spotting
3: necrosis of leaf margin even on emerged leaves
4: phytotoxicity apparent with growth inhibition
5: completely withered.

The test results are shown in Tables 2 and 3.

TABLE 2

Test crop: Cucumber
Test pest: *Aphis gossypii*

| Formulation | Dosage of active ingredient mg/plant | Control efficacy (%) | | | Phytotoxicity |
|---|---|---|---|---|---|
| | | 7th day | 14th day | 21st day | |
| Paste I | 6 | 100 | 99.7 | 99 | 0 |
| Paste II | 6 | 100 | 100 | 99.5 | 0 |
| Paste III | 6 | 100 | 100 | 99.7 | 0 |
| Paste IV | 6 | 100 | 95 | 91 | 0 |
| Paste V | 6 | 100 | 98 | 92 | 0 |
| Comparative Example 1 | 6 | 100 | — | — | 5 |
| Comparative Example 2 | 6 | 100 | 99 | 94 | 4 |
| Comparative Example 3 | 6 | 72 | 68 | 65 | 0 |
| Untreated | — | 0 | 0 | 0 | 0 |
| Number of pests/plant (217 heads before the treatment) | | 250 | 448 | 521 | |

TABLE 3

Test crop: Eggplant
Test pest: *Myzus persicae*

| Formulation | Dosage of active ingredient mg/plant | Control efficacy (%) 7th day | 14th day | 21st day | Phytotoxicity |
|---|---|---|---|---|---|
| Paste I | 6 | 99.8 | 100 | 99 | 0 |
| Paste II | 6 | 100 | 100 | 99.7 | 0 |
| Paste III | 6 | 100 | 100 | 99.5 | 0 |
| Paste IV | 6 | 99.5 | 99 | 95 | 0 |
| Paste V | 6 | 100 | 89 | 85 | 0 |
| Comparative Example 1 | 6 | 99.8 | 100 | — | 5 |
| Comparative Example 2 | 6 | 99 | 98 | 98 | 4 |
| Comparative Example 3 | 6 | 54 | 68 | 62 | 0 |
| Untreated | — | 0 | 0 | 0 | 0 |
| Number of pests/plant (125 heads before the treatment) | | 282 | 412 | 401 | |

Example C Efficacy tests on vegetables against aphids

Test compounds d: Imidacloprid e: Compound A f: Compound B

The test compounds were formulated to pasty formulations by intimately mixing the components.

Tested crops: Cucumber (var. Suyo) and eggplant (var. Senryo ni gou) The vegetables at the growth stage of 8 leaves were used in this test.

Pest species: Aphis gossypii (wild strain) for cucumber and Myzus persicae (organophosphorus and carbamate insecticides resistant strain) for eggplant were used in this test.

Plot size and replications: Two plants planted in one pot (15 cm in diameter) per plot and tvo replications.

Date of application: In the beginning of October

Application method: The same as adopted in Example B.

Evaluation method: The same as adopted in Example B.

The test results are shown in Tables 4 and 5.

TABLE 4

Test crop: Cucumber
Test pest: *Aphis gossypii*

| Formulation | Dosage of active ingredient mg/plant | Control efficacy (%) 7th day | 14th day | 21st day | Phytotoxicity |
|---|---|---|---|---|---|
| d | 6 | 100 | 99.7 | 99 | 0 |
| | 3 | 100 | 98 | 96 | 0 |
| | 1 | 100 | 95 | 94 | 0 |
| e | 6 | 100 | 98 | 92 | 0 |
| | 3 | 99.5 | 95 | 90 | 0 |
| | 1 | 99 | 90 | 88 | 0 |
| f | 6 | 100 | 95 | 91 | 0 |
| | 3 | 100 | 92 | 88 | 0 |
| | 1 | 100 | 89 | 75 | 0 |

TABLE 4-continued

Test crop: Cucumber
Test pest: *Aphis gossypii*

| Formulation | Dosage of active ingredient mg/plant | Control efficacy (%) 7th day | 14th day | 21st day | Phytotoxicity |
|---|---|---|---|---|---|
| Untreated | — | 0 | 0 | 0 | 0 |
| Number of pests/plant (217 heads before the treatment) | | 250 | 448 | 521 | |

TABLE 5

Test crop: Eggplant
Test pest: *Myzus persicae*

| Formulation | Dosage of active ingredient mg/plant | Control efficacy (%) 7th day | 14th day | 21st day | Phytotoxicity |
|---|---|---|---|---|---|
| d | 6 | 99.8 | 100 | 99 | 0 |
| | 3 | 99.7 | 100 | 98 | 0 |
| | 1 | 99 | 99.7 | 97 | 0 |
| e | 6 | 99.5 | 99 | 95 | 0 |
| | 3 | 89 | 95 | 91 | 0 |
| | 1 | 85 | 92 | 85 | 0 |
| f | 6 | 100 | 89 | 85 | 0 |
| | 3 | 100 | 89 | 82 | 0 |
| | 1 | 99 | 87 | 78 | 0 |
| Untreated | — | 0 | 0 | 0 | 0 |
| Number of pests/plant (125 heads before the treatment) | | 282 | 412 | 401 | |

We claim:

1. A pasty composition for the control of animal pests and fungal diseases on plants, which composition consists of
   A) from about 1 to 50 per cent by weight of the composition of at least one pesticidally or fungicidally active compound selected from the group consisting of
   1-(6-chloro-3-pyridylmethyl)-N-nitro-imidazolidin-2-ylideneamine,
   N-cyano-N'-(2-chloro-5-pyridylmethyl)-N'-methyl acetoamidine,
   1-[N-(6-chloro-3-pyridylmethyl)-N-ethylamino]-1-methylamino-2-nitro-ethylene,
   1-(2-chloro-5-pyridylmethyl)-3,5-dimethyl-2-nitroimino-hexahydro-1,3,5-triazine,
   1-(2-chloro-5-thiazolylmethyl)-3,5-dimethyl-2-nitroimino-hexahydro-1,3,5-triazine,
   O,O-dimethyl O-3-methyl-4-(methylsulfinyl)-phenyl phosphorothioate,
   trans-1,4,5,6-tetrahydro-1-methyl-2-[2-(3-methyl-2-thienyl)-vinyl]-pyrimidine tartrate,
   (−)-(S)-2,3,5,6-tetrahydro-6-phenylimidazo[2,1-b]-thiazole hydrochloride,
   1-(4-chlorophenoxy)-3,3-dimethyl-1-(1,2,4-triazol-1-yl)-2-butanone,
   all-rac-1-(biphenyl-4-yl oxy)-3,3-dimethyl-1-(1 H-1,2,4-triazol-1-yl)-butan-2-ol,
   2-p-chlorophenyl-2-(1 H-1,2,4-triazol-1-yl-methyl)-hexane nitrile,
   (R,S)-2-(2,4-dichlorophenyl)-1-(1 H-1,2,4-triazol-1-yl)-hexan-2-ol, 1-[2-(2,4-dichlorophenyl)-4-propyl-1,3-dioxolane-2-yl-methyl]-1 H-1,2,4-triazole,
(E)-4-chloro-α,α,α-trifluoro-N-(1-imidazol-1-yl-2-propoxyethylidene)-O-toluidine,
N-propyl-N-[2-(2,4,6-trichlorophenoxy)-ethyl]-imidazol-1-yl carboxamide, pent-4-enyl N-furfuryl-N-imidazol-1-yl carbonyl-DL-homoalaninate,
2,4'-dichloro-α-(pyrimidine-5-yl)-benzhydryl alcohol,
(E)-(R,S)-1-(4-chlorophenyl)-4,4-dimethyl-2-(1 H-1,2,4-triazol-1-yl)-1-pentene-3-ol,
(E)-(S)-1-(4-chlorophenyl)-4,4-dimethyl-2-(1 H-1,2,4-triazol-1-yl)-penta-1-ene-3-ol,
(R,S)-1-(4-chlorophenyl)-4,4-dimethyl-3-(1 H-1,2,4-triazol-1-ylmethyl)-pentan-3-ol,
2',4'-dichloro-2-(3-pyridyl)-acetophenone (E,Z)-O-methyloxime,
1,4-bis-(2,2,2-trichloro-1-formamidoethyl)-piperazine,
(2RS, 3RS)-1-(4-chlorophenyl)-4,4-dimethyl-2-(1 H-1,2,4-triazol-1-yl)-pentan-3-ol,
(+)-cis-4-[3-(4-tert-butylphenyl)-2-methylpropyl]-2,6-dimethyl-morpholine, and
2-(4-fluorophenyl)-2-(1,2,4-triazole-2-ylmethyl)-3-(2-chlorophenyl)-epoxy-ethane, B) an adjuvant selected from the group consisting of
  i) one or more liquid adjuvants selected from the group consisting of sorbitan monolaurate, polyoxyethylene sorbitan monolaurate, polyethylene glycol (#200) and polyethylene glycol (#400); or
  ii) one or more pasty adjuvants selected from the group consisting of polyethylene glycol oleate, polyoxyethylene lanolin, and polyethylene bees wax; or
  iii) one or more solid adjuvants selected from the group consisting of polyethylene glycol (#1000) and cellulose;

C) optionally at least one excipient selected from the group consisting of lignin, lignin derivatives and mineral materials, and the concentration of (B) plus (C) ranging from about 50 to 99 per cent by weight of the compositions; and D) optionally water.

2. A method for the control of animal pests and fungal diseases on plants, which comprises treating the surfaces of the plants with a composition according to claim 1.

3. A method according to claim 2, wherein the plants to be treated are fruit vegetables, flowers, ornamental plants or trees.

4. Pasty composition according to claim 1, wherein the pesticidally or fungicidally active compound A) is selected from the group consisting of:
  1-(6-chloro-3-pyridylmethyl)-N-nitro-imidazolidin-2-ylideneamine;
  N-cyano-N-(2-chloro-5-pyridylmethyl)-N'-methyl acetoamidine;
  1-[N-(6chloro-3-pyridylmethyl)-N-ethylamino]-1-methylamino-2-nitroethylene;
  O,O-dimethyl O-3-methyl-4-(methylsulfinyl)-phenyl phosphorothioate;
  trans-1,4,5,6-tetrahydro-1-methyl-2[2-(3-methyl-2-thienyl)-vinyl]-pyrimidine tartrate;
  (−)-(S)-2,3,5,6-tetrahydro-6-phenylimidazo[2,1-b]-thiazol hydrochloride; and
  1-(4-chlorophenoxy)-3,3-dimethyl-1-(1,2,4-triazol-1-yl)-2-butanone.

5. The method according to claim 1, wherein the pesticidally or fungicidally active compound A) is selected from the group consisting of:
  1-(6-Chloro-3-pyridylmethyl)-N-nitro-imidazolidin-2-ylideneamine;
  N-cyano-N-(2-chloro-5-pyridylmethyl)-N'-methyl acetoamidine;
  1-[N-(6-chloro-3-pyridylmethyl)-N-ethylamino]-1-methylamino-2-nitroethylene;
  O,O-dimethyl O-3-methyl-4-(methylsulfinyl)-phenyl phosphorothioate;
  trans-1,4,5,6-tetrahydro-1-methyl-2[2-(3-methyl-2-thienyl)-vinyl]-pyrimidine tartrate;
  (−)-(S)-2,3,5,6-tetrahydro-6-phenylimidazo[2,1-b]-thiazol hydrochloride; and
  1-(4-chlorophenoxy)-3,3-dimethyl-1-(1,2,4-triazol-1-yl)-2-butanone.

* * * * *